(12) United States Patent
Adolf et al.

(10) Patent No.: US 11,460,411 B2
(45) Date of Patent: Oct. 4, 2022

(54) PROCESS AND APPARATUS FOR INSPECTING MICRONEEDLE ARRAYS

(71) Applicant: KINDEVA DRUG DELIVERY L.P., St. Paul, MN (US)

(72) Inventors: Jeffrey P. Adolf, St. Paul, MN (US); Steven P. Floeder, St. Paul, MN (US); Jason P. Smith, St. Paul, MN (US); Steven R. Dreger, St. Paul, MN (US)

(73) Assignee: Kindeva Drug Delivery L.P., Woodbury, MN (US)

( * ) Notice: Subject to any disclaimer, the term of this patent is extended or adjusted under 35 U.S.C. 154(b) by 0 days.

(21) Appl. No.: 15/734,013

(22) PCT Filed: Jun. 13, 2019

(86) PCT No.: PCT/IB2019/054968
§ 371 (c)(1),
(2) Date: Dec. 1, 2020

(87) PCT Pub. No.: WO2019/243967
PCT Pub. Date: Dec. 26, 2019

(65) Prior Publication Data
US 2021/0215616 A1    Jul. 15, 2021

Related U.S. Application Data

(60) Provisional application No. 62/686,276, filed on Jun. 18, 2018.

(51) Int. Cl.
*G06T 7/50*    (2017.01)
*G01N 21/84*    (2006.01)
(Continued)

(52) U.S. Cl.
CPC ..... *G01N 21/8422* (2013.01); *A61M 37/0015* (2013.01); *G01B 11/0616* (2013.01);
(Continued)

(58) Field of Classification Search
CPC .............. G01N 21/8422; G01N 21/95; G01N 2021/8427; G06T 7/50; G06T 7/0004;
(Continued)

(56) References Cited

U.S. PATENT DOCUMENTS 5,440,446 A    8/1995    Shaw et al.
6,091,975 A    7/2000    Daddona et al.
(Continued)

FOREIGN PATENT DOCUMENTS

JP    2017161487 A  *  9/2017
JP    2017161487 A     9/2017
(Continued)

OTHER PUBLICATIONS

International Search Report and Written Opinion for PCT/IB2019/054968, issued by the European Patent Office dated Dec. 11, 2019; 9 pgs.

(Continued)

*Primary Examiner* — Isiaka O Akanbi
(74) *Attorney, Agent, or Firm* — Mueting Raasch Group

(57) ABSTRACT

A process of making a microneedle array comprising providing a microneedle array having a plurality of microneedles of a desired shape, illuminating at least a portion of said microneedle array that comprises at least one microneedle, capturing an observed image of said at least one microneedle using an optical device, electronically processing said observed image and determining at least one shape parameter for said at least one microneedle, accepting said microneedle array if said at least one shape parameter is within an acceptable range, thereby providing a microneedle array that comprises a known shape of the plurality of microneedles.

19 Claims, 5 Drawing Sheets

(51) Int. Cl.
*A61M 37/00* (2006.01)
*G01B 11/06* (2006.01)
*G01N 21/95* (2006.01)
*G06T 7/00* (2017.01)
*H04N 5/225* (2006.01)

(52) U.S. Cl.
CPC .......... *G01N 21/95* (2013.01); *G06T 7/0004* (2013.01); *G06T 7/50* (2017.01); *H04N 5/2256* (2013.01); *A61M 2037/0023* (2013.01); *A61M 2037/0053* (2013.01); *G01N 2021/8427* (2013.01); *G06T 2207/30108* (2013.01)

(58) Field of Classification Search
CPC ..... G06T 2207/30108; A61M 37/0015; A61M 2037/0023; A61M 2037/0053; A61M 2037/0046; A61M 2037/0061; G01B 11/0616; H04N 5/2256; A61K 9/0021
USPC .................. 356/141, 237.1–237.6; 424/422
See application file for complete search history.

(56) References Cited

U.S. PATENT DOCUMENTS

| 6,881,538 | B1 | | 4/2005 | Haddad et al. |
| 7,132,054 | B1 | * | 11/2006 | Kravitz ............. A61M 37/0015 216/87 |
| 8,414,959 | B2 | | 4/2013 | Hye-Ok et al. |
| 8,900,194 | B2 | | 12/2014 | Clarke et al. |
| 9,693,950 | B2 | | 7/2017 | Determan et al. |
| 2004/0049150 | A1 | | 3/2004 | Dalton et al. |
| 2005/0209565 | A1 | * | 9/2005 | Yuzhakov ......... A61M 37/0015 604/173 |
| 2008/0287858 | A1 | * | 11/2008 | Duan ................ A61M 37/0015 604/21 |
| 2009/0131887 | A1 | * | 5/2009 | Shiomitsu ......... A61M 37/0015 264/220 |
| 2013/0113919 | A1 | | 5/2013 | Qiao et al. |
| 2014/0066842 | A1 | * | 3/2014 | Zhang .................... A61P 43/00 604/512 |
| 2014/0066843 | A1 | * | 3/2014 | Zhang ............... A61M 37/0015 604/512 |
| 2018/0058903 | A1 | * | 3/2018 | Hu ......................... G01B 11/24 |

FOREIGN PATENT DOCUMENTS

WO 2012074576 6/2012
WO 2012122162 9/2012

OTHER PUBLICATIONS

International Preliminary Report on Patentability for PCT/IB2019/054968, issued by the International Bureau of WIPO dated Dec. 22, 2020; 7 pgs.

* cited by examiner

PROCESS AND APPARATUS FOR INSPECTING MICRONEEDLE ARRAYS

This application is the § 371 U.S. National Stage of International Application No. PCT/IB2019/054968, filed 13 Jun. 2019, which claims the benefit of U.S. Provisional Application No. 62/686,276, filed 18 Jun. 2018, the disclosures of which are incorporated by reference herein in their entireties.

FIELD

The present disclosure generally relates to microneedle arrays used to treat an area of the skin and/or to deliver an active agent to a patient and, more particularly, to equipment and methods of making such microneedle arrays.

BACKGROUND

Microneedle arrays are known in the art. Microneedle arrays have a plurality of very small microneedles that may be hollow or solid and may be coated in a material (e.g. active agent such as drug) that is to be delivered to a patient. Various shapes and arrangements of microneedles in the array are known, as well as various methods for making the microneedle arrays, such as by injection molding. In the case of coated microneedle arrays, various methods for coating a desired material onto the microneedles of a microneedle array are known. To assure proper functioning of the microneedle array in terms of penetration and delivery, it is important that the shape and any coating be as intended.

SUMMARY

It has been found that, despite known methods of manufacturing microneedle arrays and methods of effectively coating material onto a microneedle array, such arrays and coatings are susceptible to variance in the shape of the needles and amount and distribution of material coating on the individual microneedles, as well as variance between individual arrays. The present invention provides equipment and a process of making microneedle arrays wherein the process comprises providing a microneedle array having a plurality of microneedles of a desired shape, illuminating at least a portion of said microneedle array that comprises at least one microneedle, capturing an observed image of said at least one microneedle using an optical device, electronically processing said observed image and determining at least one shape parameter for said at least one microneedle, accepting said microneedle array if said at least one shape parameter is within an acceptable range, thereby providing a microneedle array that comprises a known shape of the plurality of microneedles.

The present invention is particularly useful in the difficult context of microneedle arrays coated with a material (e.g., an active agent) to be delivered from the needles. It is critical that the amount of material be as intended and the present invention provides a reliable, fast, and efficient method of determining the amount of material coating the plurality of microneedles from a single image. It also allows one to determine the distribution of material on the microneedle, which can also be important.

One aspect of the present invention can comprise a light source at a 40° angle to the surface of the coated microneedle array and an optical device above the microneedle array that is located such that a linear line from the microneedle array to the optical device is normal to the surface of the microneedle array. The light source projects light through the microneedles and the corresponding microneedle shadows are observed on the surface of the microneedle array. The image of the microneedle shadows is then processed to determine an amount of material coating the plurality of coated microneedles.

Another aspect of the present invention can comprise equipment for use in an apparatus for making a microneedle array, the apparatus comprising an optical device, a light source, and a microneedle array that comprises a plurality of microneedles with a material coating on at least one microneedle. In a preferred embodiment, the optical device is a 2D array camera. In another embodiment, the light source is a white LED with a collimated lens. The apparatus can optionally include more than one light source and/or optical device.

An additional aspect of the present invention further provides a process for inspecting microneedle arrays comprising illuminating at least a portion of a microneedle array that comprises at least one microneedle with a light source, capturing an observed image of said at least one microneedle using an optical device, electronically processing the observed image, and determining an amount of a material coating on said at least one microneedle.

DETAILED DESCRIPTION

Figure 1:
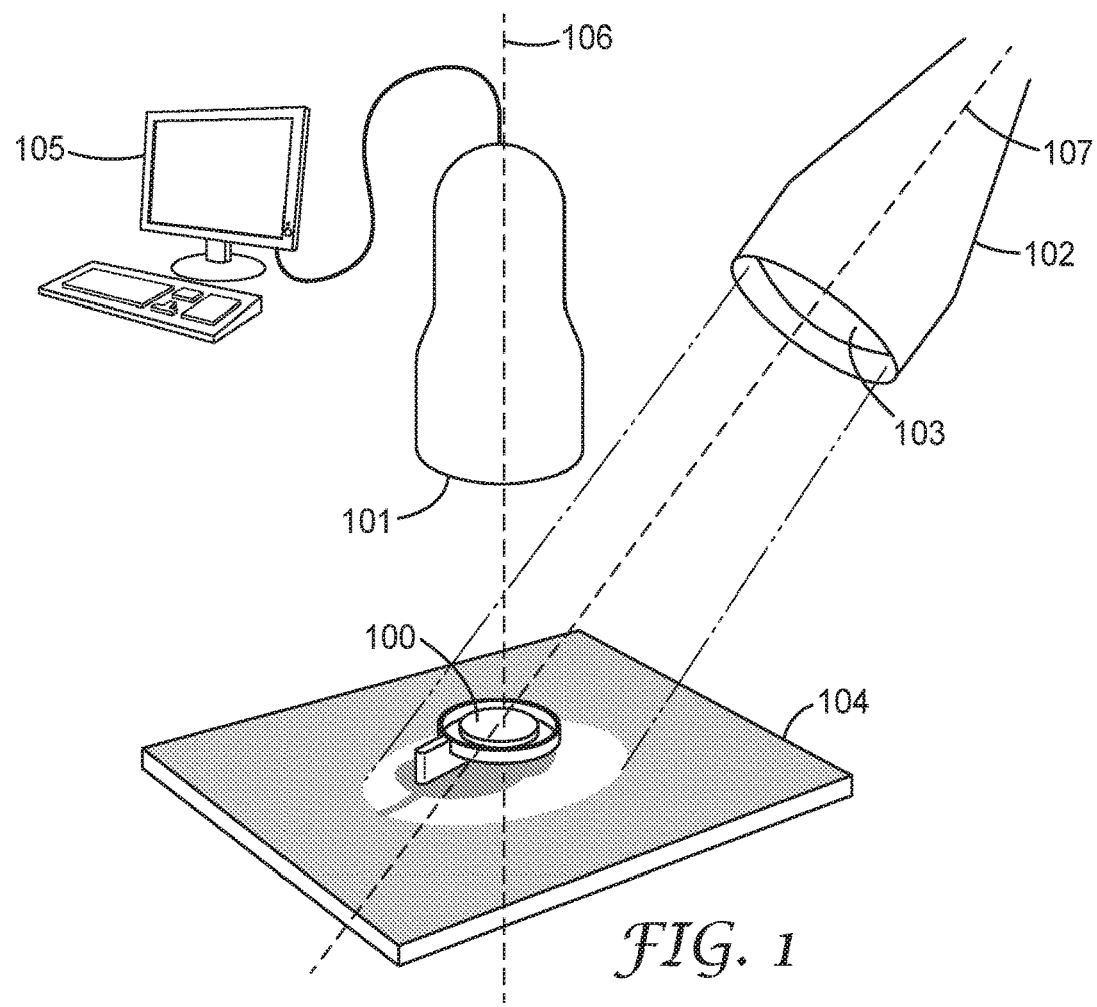
FIG. 1 is a perspective view of a microneedle array system in accordance with an embodiment of the present invention.

Throughout this disclosure, singular forms such as "a," "an," and "the" are often used for convenience; however, it should be understood that the singular forms are meant to include the plural unless the singular alone is explicitly specified or is clearly indicated by the context.

Some terms used in this application have special meanings, as defined herein. All other terms will be known to the skilled artisan, and are to be afforded the meaning that a person of skill in the art at the time of the invention would have given them.

Elements in this specification that are referred to as "common," "commonly used," and the like, should be understood to be common within the context of the articles, such as microneedles and microneedle arrays, and methods of this disclosure; this terminology is not used to mean that these features are present, much less common, in the prior art. Unless otherwise specified, only the Background section of this Application refers to the prior art.

Before any embodiments of the present disclosure are explained in detail, it is to be understood that the inventions are not limited in its application to the details of construction and the arrangement of components set forth in the following description or illustrated in the following drawings. The inventions are capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. Furthermore, terms such as "front," "rear," "top," "bottom," "upward," "downward," "under," "normal," and the like are only used to describe elements as they relate to one another, but are in no way meant to recite specific orientations of the apparatus, to indicate or imply necessary or required orientations of the apparatus, or to specify how the inventions described herein will be used, mounted, displayed, or positioned in use.

The term "transdermally," and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

Microneedle Arrays

Figure 2:
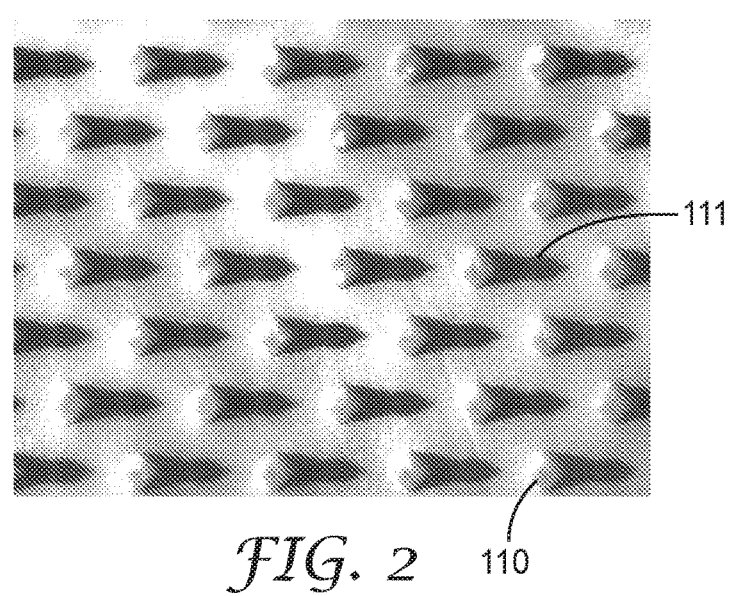
FIG. 2 is a view of a coated microneedle array imaged in accordance with an embodiment of the present invention.
Figure 7:
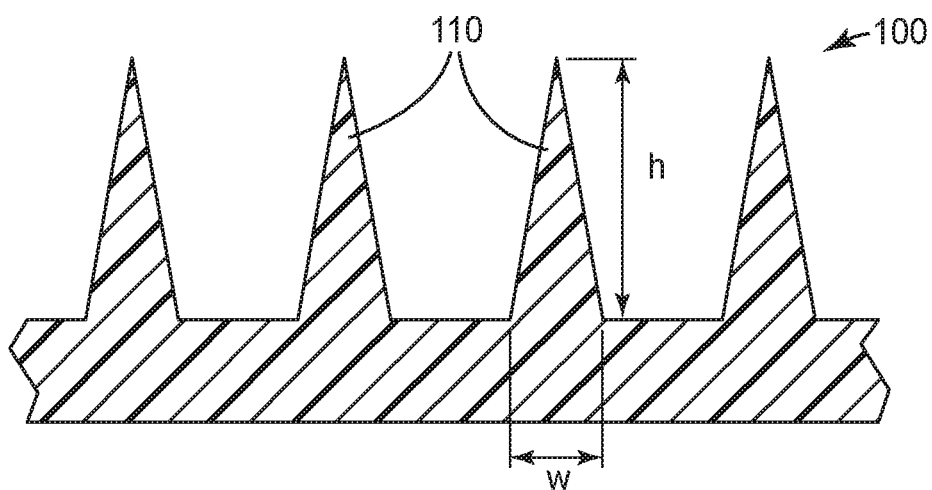
FIG. 7 is a close-up side elevational view of a microneedle array (shown with uncoated microneedles pointing upwardly).

Referring to FIGS. 2 and 7, a microneedle array assembly 100, which can also be referred to herein as a "microneedle device" or "patch," includes a plurality of microneedles 110 (or, collectively, the "microneedle army").

In some embodiments, the material to be delivered by the microneedles to the subject is an active ingredient or agent. Examples of pharmaceutically active agents (also referred to as "drugs") that can be incorporated into the applicators of the present disclosure are those capable of local or systemic effect when administered to the skin. Some examples include abalopartide, buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl, which are commercially available in the form of transdermal devices. Other examples include anti-inflammatory drugs, both steroidal (e.g., hydrocortisone, prednisolone, triamcinolone) and non-steroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-1-yl)butyl]methanesulfonamide, and acyclovir); local anesthetics (e.g., benzocaine, propofol, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatriptan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; anti-obesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, interferon-gamma, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In some embodiments, peptide therapeutic agents (natural, synthetic, or recombinant) can be delivered via the microneedles. Examples of peptide therapeutic agents that can be incorporated into the applicators of the present disclosure include parathyroid hormone (PTH), parathyroid hormone related protein (PTHrP), calcitonin, lysozyme, insulin, insulinotropic analogs, glatiramer acetate, goserelin acetate, somatostatin, octreotide, leuprolide, vasopressin, desmopressin, thymosin alpha-1, atrial natriuretic peptide (ANP), endorphin, vascular endothelial growth factor (VEGF), fibroblast-growth factor (FGF), erythropoietin (EPO), bone morphogenetic proteins (BMPs), epidermal growth factor (EFG), granulocyte colony-stimulating factor (G-CSF), granulocyte macrophage colony stimulating factor (GM-CSF), insulin-like growth factor (IGF), platelet-derived growth factor (PDGF), growth hormone release hormone (GHRH), dornase alfa, tissue plasminogen activator (tPA), urokinase, ANP clearance inhibitors, lutenizing hormone releasing hormone (LHRH), melanocyte stimulating hormones (alpha & beta MSH), pituitary hormones (hGH), adrenocorticotropic hormone (ACTH), human chorionic gonadotropin (hCG), streptokinase, interleukins (e g IL-2, IL-4, IL-10, IL-12, IL-15, IL-18), protein C, protein S, angiotensin, angiogenin, endothelins, pentigetide, brain natriuretic peptide (BNP), neuropeptide Y, islet amyloid polypeptide (IAPP), vasoactive intestinal peptide (VIP), hirudin, glucagon, oxytocin, and derivatives of any of the foregoing peptide therapeutic agents.

In some embodiments, drugs that are of a large molecular weight may be delivered transdermally. Increasing molecular weight of a drug typically can cause a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include therapeutic cancer vaccines, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, recombinant protein vaccine, DNA vaccines, polio vaccine, therapeutic cancer vaccine, herpes vaccine, human papilloma virus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Patent Application Publication No. 2004/0049150 (Dalton et al.), the disclosure of which is hereby incorporated by reference in its entirety.

In another embodiment, small-molecule drugs that are otherwise difficult or impossible to deliver by passive transdermal delivery may be used. Examples of such molecules include salt forms; ionic molecules, such as bisphosphonates, including sodium alendronate or pamedronate; and molecules with physicochemical properties that are not conducive to passive transdermal delivery.

In yet an additional embodiment, microneedle arrays can be used to deliver cosmetic materials to a subject.

Microneedle arrays useful for practicing the present disclosure can have a variety of configurations and features, such as those described in the following patents and patent applications, the disclosures of which are incorporated herein by reference in their entirety. One embodiment for the microneedle arrays include the structures disclosed in U.S. Patent Application Publication No. 2005/0261631 (Clarke et al.), which describes microneedles having a truncated tapered shape and a controlled aspect ratio. Another embodiment for the microneedle arrays includes the structures disclosed in U.S. Pat. No. 6,091,975 (Daddona et al.), which describes blade-like microprotrusions for piercing the skin.

Various embodiments of microneedles that can be employed in the microneedle arrays of the present disclosure are described in PCT Publication No. WO2012/074576 (Duan et al.), which describes liquid crystalline polymer (LCP) microneedles; and PCT Publication No. WO2012/122162 (Zhang et al.), which describes a variety of different types and compositions of microneedles that can be employed in the microneedles of the present disclosure.

In some embodiments, the microneedle material can be (or include) silicon, glass, or a metal such as stainless steel, titanium, or nickel titanium alloy. In some embodiments, the microneedle material can be (or include) a polymeric material, preferably a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Preferred types of medical grade polymeric materials include polycarbonate and LCP.

In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the microneedles can be a prepared from a dissolvable, degradable, or disintegratable material referred to herein as "dissolvable microneedles". A dissolvable, degradable, or disintegratable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In some embodiments, the microneedles can be made from (or include) a combination of two or more of any of the above-mentioned materials. For example, the tip of a microneedle may be a dissolvable material, while the remainder of the microneedle is a medical grade polymeric material.

The surface of the microneedles may be altered with a surface pre-treatment, such as a plasma treatment capable of altering surface functionality. For example, polycarbonate may be plasma treated with a nitrogen plasma to cause amide functionalization or with an oxygen plasma to cause carboxylate functionalization A combination of nitrogen and oxygen plasma treatment may be used to give a mixed surface functionality. Alternatively, the surface of the microneedles may be treated with a coating to alter the surface properties. Such a coating may be directly applied as a solid material, such as through use of heat or plasma deposition. Examples of thin layers of material cured onto the array include plasma deposited diamond-like glass films, such as those described in U.S. Pat. No. 6,881,538 (the disclosure of which is incorporated herein by reference thereto), ultraviolet polymerized acrylates, such as those described in U.S. Pat. No. 5,440,446 (the disclosure of which is incorporated herein by reference thereto), plasma deposited fluoropolymers, or any other thin layer that may be applied by conventional coating method, such as spray coating or roll coating and subsequently crosslinked using any suitable radiation. In one embodiment, a diamond-like glass film may be deposited on the microneedles and subsequently treated with an oxygen plasma to make the surface hydrophilic.

In an embodiment of the present invention, at least one microneedle of the microneedle array can be coated in a material. In an additional embodiment of the present invention, a plurality of the microneedles of the microneedle array can be coated in a material. Coating the microneedles in a material can be accomplished by bringing at least a portion of the plurality of microneedles into contact with the material coating formulation. The coating step can comprise any microneedle coating methods known in the art. For example, the formulations can be applied to the microneedles by dip-coating such as described, for example, in U.S. Pat. No. 8,414,959 (Choi et al.), U.S. Patent Application Publication No. 2014/0066842 (Zhang et al.), and U.S. Pat. No. 9,693,950 (Determan et al.), the disclosures of which are incorporated herein by reference.

Further, to improve image resolution, contrast, and comparison, it may be desirable to apply a coating of a particular color that is different than the underlying microneedle substrate. If necessary, this can be enhanced by including a dye component to either the material or on or within the microneedle material itself.

A microneedle or the plurality of microneedles in a microneedle array useful for practicing the present disclosure can have a variety of shapes that are capable of piercing the stratum corneum. In some embodiments, one or more of the plurality of microneedles can have a square pyramidal shape, triangular pyramidal shape, stepped pyramidal shape, conical shape, microblade shape, or the shape of a hypodermic needle. In some embodiments, one or more of the plurality of microneedles can have a square pyramidal shape. In some embodiments, one or more of the plurality of microneedles can have a triangular pyramidal shape. In some embodiments, one or more of the plurality of microneedles can have a stepped pyramidal shape. In some embodiments, one or more of the plurality of microneedles can have a conical shape. In some embodiments, one or more of the plurality of microneedles can have a microblade shape. In some embodiments, one or more of the plurality of microneedles can have the shape of a hypodermic needle. The shape can be symmetric or asymmetric. The shape can be truncated (for example, the plurality of microneedles can have a truncated pyramid shape or truncated cone shape). In a preferred embodiment, the plurality of microneedles in a microneedle array each have a square pyramidal shape.

In some embodiments the at least one microneedle or a plurality of microneedles in a microneedle array are hollow, but can be coated with a material to be delivered. In some embodiments, the plurality of microneedles in a microneedle array are solid microneedles (that is, the microneedles are solid throughout) and coated with material to be coated. In some embodiments, the plurality of solid microneedles in a solid microneedle array can have a square pyramidal shape, triangular pyramidal shape, stepped pyramidal shape, conical shape, or microblade shape. In some embodiments, the plurality of solid microneedles has a dual-shape, that is the needles have a first shape near the base and a second shape near the tip. In a preferred embodiment, the plurality of solid microneedles in a solid microneedle array each have a square pyramidal shape.

FIG. 7 shows a small portion of a microneedle array 100 that includes four uncoated microneedles 110. Each microneedle 110 has a height h, which is the length from the tip of the microneedle to the microneedle base at substrate. Either the height of a single microneedle 110 or the average height of all microneedles 110 on the microneedle array 100 can be referred to as the height of the microneedle, h. In some embodiments, each of the plurality of microneedles 110 (or the average of all of the plurality of microneedles) has a height of about 100 to about 3000 micrometers, in some embodiments, about 100 to about 1500 micrometers, in some embodiments, about 100 to about 1200 micrometers, and, in some embodiments, about 100 to about 1000 micrometers.

In some embodiments, each of the plurality of microneedles 110 (or the average of all of the plurality of microneedles) has a height of about 200 to about 1200 micrometers, about 200 to about 1000 micrometers, about 200 to about 750 micrometers, or about 200 to about 600 micrometers.

In some embodiments, each of the plurality of microneedles 110 (or the average of all of the plurality of microneedles) has a height of about 250 to about 1500 micrometers, about 500 to about 1000 micrometers, or about 500 to about 750 micrometers.

In some embodiments, each of the plurality of microneedles 110 (or the average of all of the plurality of microneedles) has a height of about 800 to about 1400 micrometers.

In some embodiments, each of the plurality of microneedles 110 (or the average of all of the plurality of microneedles) has a height of about 500.

In some embodiments, each of the plurality of microneedles 110 (or the average of all of the plurality of microneedles 110) has a height of less than about 3000 micrometers. In other embodiments, each of the plurality of microneedles 110 (or the average of all of the plurality of microneedles 110) has a height of less than about 1500 micrometers. In still other embodiments, each of the plurality of microneedles 110 (or the average of all of the plurality of microneedles 110) has a height of less than about 1200 micrometers. In yet still other embodiments, each of the plurality of microneedles 110 (or the average of all of the plurality of microneedles 110) has a height of less than about 1000 micrometers. In further embodiments, each of the plurality of microneedles 110 (or the average of all of the plurality of microneedles 110) has a height of less than about 750 micrometers. In still further embodiments, each of the plurality of microneedles 110 (or the average of all of the plurality of microneedles) has a height of less than about 600 micrometers.

In some embodiments, each of the plurality of microneedles 110 (or the average of all of the plurality of microneedles 110) has a height of at least about 100 micrometers. In other embodiments, each of the plurality of microneedles 110 (or the average of all of the plurality of microneedles 110) has a height of at least about 200 micrometers. In still other embodiments, each of the plurality of microneedles 110 (or the average of all of the plurality of microneedles 110) has a height of at least about 250 micrometers. In further embodiments, each of the plurality of microneedles 110 (or the average of all of the plurality of microneedles 110) has a height of at least about 500 micrometers. In still further embodiments, each of the plurality of microneedles 110 (or the average of all of the plurality of microneedles 110) has a height of at least about 800 micrometers.

A single microneedle 110 or the plurality of microneedles 110 in a microneedle array 100 can also be characterized by their aspect ratio. The aspect ratio of a microneedle is the ratio of the height of the microneedle, h to the width (at the base of the microneedle), w (as shown in FIG. 7). The aspect ratio can be presented as h:w. In some embodiments, each of the plurality of microneedles 110 (or the average of all the plurality of microneedles 110) has (have) an aspect ratio in the range of 2:1 to 5:1. In some of these embodiments, each of the plurality of microneedles 110 (or the average of all of the plurality of microneedles 110) has (have) an aspect ratio of at least 3:1.

In some embodiments, the microneedle array 100 contains about 100 to about 1500 microneedles 110 per $cm^2$ of the microneedle array 100.

In some embodiments, the microneedle array 100 contains about 200 to about 500 microneedles 110 per $cm^2$ of the microneedle array 100.

In some embodiments, the microneedle array 100 contains about 300 to about 400 microneedles 110 per cm² of the microneedle array 100.

In some embodiments, each of the plurality of microneedles 110 (or the average of all of the plurality of microneedles 110) in a microneedle array 100 can penetrate into the skin to a depth of about 50 to about 1500 micrometers, about 50 to about 400 micrometers, or about 50 to about 250 micrometers.

In some embodiments, each of the plurality of microneedles 110 (or the average of all of the plurality of microneedles 110) in a microneedle array 100 can penetrate into the skin to a depth of about 100 to about 400 micrometers, or about 100 to about 300 micrometers.

In some embodiments, each of the plurality of microneedles 110 (or the average of all of the plurality of microneedles 110) in a microneedle array 100 can penetrate into the skin to a depth of about 150 to about 1500 micrometers, or about 800 to about 1500 micrometers.

In some embodiments, each of the plurality of microneedles 110 (or the average of all of the plurality of microneedles 110) in a microneedle array 100 can penetrate into the skin to a depth of about 400 to about 800 micrometers.

For all of the above embodiments, it will be appreciated that the depth of penetration (DOP) of each of the plurality of microneedles 110 (or the average of all of the plurality of microneedles 110) in a microneedle array 100 may not be the full length of the microneedles themselves.

In some embodiments, the microneedle array 100 according to the present disclosure can be in the form of a patch. Microneedles 110 can be arranged in any desired pattern or distributed over the patch randomly. As shown in FIG. 2, microneedles 110 are arranged in uniformly spaced rows. When arranged in rows, the rows can be arranged so that microneedles 110 are aligned or offset. In some embodiments (not shown), microneedles 110 can be arranged in a polygonal pattern such as a triangle, square, rectangle, pentagon, hexagon, heptagon, octagon, or trapezoid. In other embodiments (not shown), microneedles 110 can be arranged in a circular or oval pattern.

In some embodiments, the surface area of the array 100 covered with microneedles 110 is about 0.1 cm² to about 20 cm². In some of these embodiments, the surface area of the array 100 covered with microneedles 110 is about 0.5 cm² to about 5 cm². In some other of these embodiments, the surface area of the array 100 covered with microneedles 110 is about 1 cm² to about 3 cm². In still other of these embodiments, the surface area of the array 100 covered with microneedles 110 is about 1 cm² to about 2 cm².

In some embodiments, the microneedles 110 of the present disclosure can be disposed over substantially the entire surface of the array 100. In other embodiments (not shown), a portion of the substrate may not be provided with microneedles 110 (that is, a portion of the array is non-structured). In some of these embodiments, the non-structured surface has an area of more than about 1 percent and less than about 75 percent of the total area of the device surface that faces the skin surface. In another of these embodiments, the non-structured surface has an area of more than about 0.65 cm² (0.10 square inch) to less than about 6.5 cm² (1 square inch).

In some embodiments, the average spacing between adjacent microneedles 110 (as measured from microneedle tip to microneedle tip) is between about 200 micrometers and about 2000 micrometers. In other embodiments, the average spacing between adjacent microneedles 110 is between about 200 micrometers and about 600 micrometers. In still other embodiments, the average spacing between adjacent microneedles 110 is between about 200 micrometers and about 300 micrometers. In yet still other embodiments, the average spacing between adjacent microneedles 110 is between about 500 micrometers and about 600 micrometers.

In some embodiments, the average spacing between adjacent microneedles 110 (as measured from microneedle tip to microneedle tip) is greater than about 200 micrometers. In other embodiments, the average spacing between adjacent microneedles 110 is greater than about 500 micrometers.

In some embodiments, the average spacing between adjacent microneedles 110 is less than about 2000 micrometers. In other embodiments, the average spacing between adjacent microneedles 110 is less than about 1000 micrometers. In still other embodiments, the average spacing between adjacent microneedles 110 is less than about 600 micrometers. In yet still other embodiments, the average spacing between adjacent microneedles 110 is less than about 300 micrometers.

The microneedle arrays 100 can be manufactured in any suitable way such as by (but not limited to) injection molding, compression molding, metal injection molding, stamping, photolithography, or extrusion.

Optical Method

FIG. 1 shows an embodiment of the invention relates to a process of making microneedle arrays 100 with a known amount of material coating the microneedles 110. The process involves optically determining the shape and/or amount of material coating microneedles 110, which, among other attributes, enables non-destructive, in-line quality control of microneedle arrays. Various embodiments include, but are not are not limited to, the following paragraphs.

Referring to FIG. 1, the process includes illuminating a microneedle array 100 with a light source 102 illuminates the individual microneedles array. Suitable light sources are those known in the art. Preferentially, the light source is capable of illuminating at least a portion of the microneedle array 100. The light source can be ambient background light. Particularly useful light sources comprise a broad spectrum white light, a monochromatic light, a laser, a LED, an incandescent light, a fluorescent light, an OLED, or a combination thereof. The light source 102 may have a lens 103. The light emitted from the light source may be any suitable wavelength. The light emitted from the light source may be in the visible spectrum. The light emitted from the light source may be outside the visible spectrum. Suitable light may comprise broad spectrum light, white light, monochromatic light, collimated light, or a combination thereof. The incident light intensity is strong enough as to illuminate at least a portion of the microneedle array. In some embodiments, it may be beneficial to use more than one light source. Preferentially, the light source projects light through the microneedle array at an acute angle defined by a linear line 107 from the light source 102 to the surface of the microneedle array 100. In other embodiments the acute angle is at least 89°, at least 80°, at least 70°, at least 60°, at least 45°, at least 30°, between about 30° and about 90°, between about 5° and about 85°, between about 10° and 75°, between about 20° and 60°, between about 30° and 50°, about 80°, about 70°, about 60°, about 50°, and more preferably about 40° to the microneedle array 100. In an additional embodiment, the light source is positioned so that the shadows of at least one microneedle do not project onto neighboring microneedles. In another embodiment, the light source is positioned so that the shadows of a plurality of microneedles do not project onto neighboring microneedles.

In an embodiment, an image of the microneedle array is captured using a device which can be an optical device 101. Preferentially, the optical device 101 can be any suitable device for capturing an image. Particularly, a spectroscope can be used as the optical device 101. Particularly, a CCD camera can be used as the optical device 101. Particularly, a 2D video camera can be used as the optical device 101. Particularly, a 2D array camera can be used as the optical device 101. Particularly, a 1D linescan camera can be used as the optical device 101. The image capturing device can be equipped with a telecentric lens. Particularly, the telecentric lens can magnify the observed image. The magnification can be any suitable magnification for capturing an image. Particularly, the magnification can be 1×, 2×, 3×, 4×, 5×, or greater than 5×. In a particular embodiment, the image capturing device is a 2D array camera with a 2× magnification telecentric lens. In some embodiments, it may be beneficial to use more than one camera optical device. In some embodiments, the optical device is connected to an image processing device. A particular image processing device includes a computer 105.

The microneedle array is rotated as to have any orientation with respect to a linear line 107 from the light source 102 to the microneedle array 100. Particularly, an orientation which maximizes the distance between microneedles in the direction of a linear line 107 from the light source 102 to the microneedle array 100. In some embodiments, the microneedle array 100 is rotated as to present the widest cross-sectional area of the individual microneedles to the incident light.

The observed image can be the microneedle array with a plurality of coated microneedles. In another embodiment, the observed image can be the microneedle array with at least one coated microneedle from which at least one microneedle shadow is observed. In another embodiment, the at least one microneedle is a plurality of microneedles. In another embodiment, the observed image is a shadow from an individual coated microneedle. In yet another embodiment, the observed image is all the coated microneedles with an analogous number of microneedle shadows projected on the surface of the microneedle array. In an additional embodiment, more than one coated microneedle array can be imaged.

In an additional embodiment the observed image can be the microneedle array with a plurality of uncoated microneedles. In another embodiment, the observed image can be the microneedle array with at least one uncoated microneedles from which at least one shadow is observed. In another embodiment, the at least one microneedle is a plurality of microneedles. In another embodiment, the observed image is a shadow from an individual uncoated microneedle. In yet another embodiment, the observed image is all the uncoated microneedles with an analogous number of microneedle shadows projected on the surface of the microneedle array. In an additional embodiment, more than one uncoated microneedle array can be imaged.

A shape parameter can be determined from the observed image. Multiple shape parameters can be determined from a single observed image. Shape parameters that can be determined include the microneedle height, width, angle, spacing, base area, and possible imperfections such as truncated needles and non-uniform shape. In embodiments with coated microneedles, the shape of the coating and the position of the coating on the plurality of microneedles can be determined.

In some embodiments, the optical device 101 is positioned above the microneedle array and such that a linear line 106 from the optical device 101 through the microneedle array 100 is at an angle of at least 40°, 50°, 60°, 70°, 80°, 90° to the array 100. Particularly, the optical device 101 is positioned above the microneedle array 100 and a linear line 106 from the optical device 101 through the microneedle array 100 is normal to the array 100.

In some embodiments, the process may further comprise processing the observed image using one or more image processing techniques. Useful image processing techniques include but are not limited to binarizing, horizontal flat-fielding, unsharp masking, linear deconvolution, non-linear deconvolution, blind deconvolution, blob extraction, binary threshold, or combinations thereof.

Electronically comparing a shape parameter from an observed image to an acceptable shape parameter can be performed digitally or by a person. Exemplary digital devices include computers. The process of comparing a shape parameter from an observed image to an acceptable shape parameter can be performed by any method known in the art. In some embodiments, an acceptable deviation of the observed shape parameter from the acceptable shape parameter can be no greater than 1%, no greater than 3%, no greater than 5%, no greater than 7%, no greater than 10%, no greater than 15%, no greater than 20%, no greater than 25%, or even no greater than 50%.

LIST OF EXEMPLARY EMBODIMENTS

The following embodiments are meant to be illustrative, and are not intended to be limiting unless otherwise specified.

1. A process of making a microneedle array comprising:
providing a microneedle array having a plurality of microneedles of a desired shape;
illuminating at least a portion of said microneedle array that comprises at least one microneedle;
capturing an observed image of said at least one microneedle using an optical device;
electronically processing said observed image and determining at least one shape parameter for said at least one microneedle;
accepting said microneedle array if said at least one shape parameter is within an acceptable range;
thereby providing a microneedle array that comprises a known shape of the plurality of microneedles.

2. The process of embodiment 1, wherein the at least one microneedle is coated with a material.

3. The process of embodiment 2, further comprising determining an amount of material on said at least one microneedle.

4. The process of embodiment 2 or 3, comprising a known amount of material on at least one individual microneedle of the microneedle array.

5. The process of any previous embodiment, wherein the microneedles of the microneedle array comprise a silicon, glass, metal, polymeric material, dissolvable material, or a combination thereof.

6. The process of any previous embodiment, wherein one or more of the microneedles have a square pyramidal shape, triangular pyramidal shape, stepped pyramidal shape, conical shape, microblade shape, hypodermic needle shape, or a combination thereof.

7. The process of any previous embodiment, wherein the microneedles are capable of piercing a stratum corneum of a subject.

8. The process of any previous embodiment, wherein each of the plurality of microneedles has a height of about 100 to about 3000 micrometers.

9. The process of any previous embodiment, wherein each of the plurality of microneedles has an aspect ratio of 2:1 to 5:1.

10. The process of any previous embodiment, wherein the microneedle array comprises about 100 to about 1500 microneedles per $cm^2$ of the microneedle array.

11. The process of any previous embodiment, wherein each of the plurality of microneedles in the microneedle array can penetrate a skin of a subject to a depth of about 50 to about 1500 micrometers.

12. The process of embodiment 2 or 3, wherein said material coating the plurality of microneedles comprises a drug agent.

13. The process of any previous embodiment, wherein the microneedle array is disposed on a patch.

14. The process of any previous embodiment, wherein the microneedle array comprises a microneedle-containing portion and a microneedle-free portion, and wherein the microneedle-containing portion has a surface area on the microneedle array of about 0.1 $cm^2$ to about 20 $cm^2$.

15. The process of any previous embodiment, wherein the average spacing between adjacent microneedles of the microneedle array is between about 200 micrometers and about 2000 micrometers.

16. The process of any previous embodiment, wherein the step of illuminating further comprises illuminating with a directed light source.

17. The process of any previous embodiment, wherein the step of illuminating further comprises illuminating with collimated light source.

18. The process of any previous embodiment, wherein the step of illuminating further comprises illuminating with broadband white light source.

19. The process of any one of embodiments 16 to 18, wherein the light source is a LED with a collimated lens.

20. The process of any one of embodiments 16 to 19, wherein the light source projects light through the microneedle array at an acute angle of about 10° to 75° to a surface of the microneedle array.

21. The process of any one of embodiments 16 to 20, wherein the light source projects light through the microneedle array at an acute angle of about 30° to 50° to a surface of the microneedle array.

22. The process of any previous embodiment, wherein the observed image is at least one shadow projected onto a surface of the microneedle array from said at least one microneedle.

23. The process of any previous embodiment, wherein the observed image is all the microneedles with an analogous number of microneedle shadows projected on a surface of the microneedle array.

24. The process of any previous embodiment, wherein shadows from said at least one microneedle do not project onto neighboring microneedles.

25. The process of any previous embodiment, wherein the optical device comprises a spectroscope.

26. The process of any previous embodiment, wherein the optical device comprises a CCD camera.

27. The process of any previous embodiment, wherein the optical device comprises a 2D array camera.

28. The process of any previous embodiment, wherein the optical device comprises a 2D array camera with a telecentric lens.

29. The process of any previous embodiment, wherein the optical device comprises a 2D array camera with a 2× magnification telecentric lens.

30. The process of any one of embodiments 1 to 25, wherein the optical device comprises a 1D linescan camera.

31. The process of any previous embodiment, wherein the optical device is positioned above the microneedle array and a linear line from the optical device through the microneedle array is normal to the array.

32. The process of any previous embodiment, wherein the step of electronically processing said observed image and determining at least one shape parameter further comprises calculating the difference between a theoretical shape of an individual microneedle and an observed shape of the individual microneedle.

33. The process of embodiment 32, wherein the theoretical shape of the individual microneedle is digitally generated.

34. The process of any previous embodiment, wherein the observed image is an 8-bit to 16-bit grayscale image.

35. The process of embodiment 34, further comprising horizontally flat-fielding the observed image to account for variable background intensity.

36. The process of embodiment 34 or 35, further comprising an image sharpening step.

37. The process of any one of embodiments 34 to 36, wherein the image sharpening step comprises an unsharp masking technique.

38. The process of any one of embodiments 34 to 36, wherein the image sharpening step comprises a non-linear deconvolution filter.

39. The process of any one of embodiments 34 to 38, further comprising a binary threshold which segments the plurality of microneedle shadows from said surface on the microneedle array.

40. The process of any one of embodiments 34 to 39, further comprising a blob extraction algorithm to isolate an individual microneedle shadow.

41. The process of embodiment 3, wherein the step of determining an amount of material on said at least one microneedle further comprises;
    defining a coated region from a shadow of an individual microneedle;
    mathematically rotating the coated region around a microneedle tip's central axis to form a solid of revolution;
    calculating an amount of a first material comprising the solid of revolution;
    calculating an amount of a second material comprising an underlying microneedle structure for the coated region;
    subtracting the amount of the second material from the first material;
    thereby determining the amount of said material on said at least one microneedle.

42. The process of any previous embodiment, wherein said shape parameter is at least one of microneedle height, width, angle, spacing, base area, or combinations thereof.

43. An apparatus for inspecting a microneedle array comprising:
    an optical device;
    a light source; and
    a microneedle array comprising a plurality of microneedles with a material coating on at least one microneedle;

44. The apparatus of embodiment 43, further comprising an image processing device.

45. The apparatus of embodiment 44, wherein the image processing device is a computer.

46. The apparatus of any one of embodiments 43 to 45, further comprising a surface on which the microneedle array is imaged.

47. The apparatus of any one of embodiments 43 to 46, wherein the optical device is a 2D array camera.

48. The apparatus of any one of embodiments 43 to 47, wherein the light source is a white LED with a collimated lens.

49. A process of inspecting a microneedle array comprising:
   illuminating at least a portion of a microneedle array that comprises at least one microneedle with a directed light source;
   capturing an observed image of said at least one microneedle using an optical device;
   electronically processing the observed image; and
   determining an amount of a material coating on said at least one microneedle.

50. The process of embodiment 49, wherein the light source is a white LED.

51. The process of embodiment 49 or 50, wherein the observed image is at least one microneedle with at least one microneedle shadow projected on a surface of the microneedle array.

52. The process of any one of embodiments 49 to 51, wherein the optical device is a 2D array camera.

53. The process of any one of embodiments 49 to 52, wherein the step of determining an amount of material on said at least one microneedle further comprises;
   defining a coated region from a shadow of an individual microneedle;
   mathematically rotating the coated region around a microneedle tip's central axis to form a solid of revolution;
   calculating an amount of a first material comprising the solid of revolution;
   calculating an amount of a second material comprising an underlying microneedle structure for the coated region;
   subtracting the amount of the second material from the first material;
   thereby determining the amount of said material on said at least one microneedle.

54. A process of making a microneedle array comprising:
   providing a microneedle array having a plurality of microneedles of a desired shape;
   illuminating at least a portion of said microneedle array that comprises a plurality of microneedles;
   capturing an observed image of said plurality of microneedles using an optical device;
   electronically processing said observed image and determining at least one shape parameter for said plurality of microneedles;
   accepting said microneedle array if said at least one shape parameter is within an acceptable range;
   thereby providing a microneedle array that comprises a known shape of the plurality of microneedles.

55. The process of embodiment 54, wherein the plurality of microneedles is coated with a material.

56. The process of embodiment 55, further comprising determining an amount of material on said plurality of microneedles.

57. The process of embodiment 55 or 56, comprising a known amount of material on at least one individual microneedle of the microneedle array.

58. The process of any one of embodiments 54 to 57, wherein the microneedles of the microneedle array comprise a silicon, glass, metal, polymeric material, dissolvable material, or a combination thereof.

59. The process of any one of embodiments 54 to 58, wherein at least one of the microneedles have a square pyramidal shape, triangular pyramidal shape, stepped pyramidal shape, conical shape, microblade shape, hypodermic needle shape, or a combination thereof.

60. The process of any one of embodiments 54 to 59, wherein the microneedles are capable of piercing a stratum corneum of a subject.

61. The process of any one of embodiments 54 to 60, wherein each of the plurality of microneedles has a height of about 100 to about 3000 micrometers.

62. The process of any one of embodiments 54 to 61, wherein each of the plurality of microneedles has an aspect ratio of 2:1 to 5:1.

63. The process of any one of embodiments 54 to 62, wherein the microneedle array comprises about 100 to about 1500 microneedles per $cm^2$ of the microneedle array.

64. The process of any one of embodiments 54 to 63, wherein each of the plurality of microneedles in the microneedle array can penetrate a skin of a subject to a depth of about 50 to about 1500 micrometers.

65. The process of embodiment 55 or 56, wherein said material coating the plurality of microneedles comprises a drug agent.

66. The process of any one of embodiments 54 to 65, wherein the microneedle array is disposed on a patch.

67. The process of any one of embodiments 54 to 66, wherein the microneedle array comprises a microneedle-containing portion and a microneedle-free portion, and wherein the microneedle-containing portion has a surface area on the microneedle array of about 0.1 $cm^2$ to about 20 $cm^2$.

68. The process of any one of embodiments 54 to 67, wherein the average spacing between adjacent microneedles of the microneedle array is between about 200 micrometers and about 2000 micrometers.

69. The process of any one of embodiments 54 to 68, wherein the step of illuminating further comprises illuminating with a directed light source.

70. The process of any one of embodiments 54 to 69, wherein the step of illuminating further comprises illuminating with collimated light source.

71. The process of any one of embodiments 54 to 70, wherein the step of illuminating further comprises illuminating with broadband white light source.

72. The process of any one of embodiments 69 to 71, wherein the light source is a LED with a collimated lens.

73. The process of any one of embodiments 69 to 72, wherein the light source projects light through the microneedle array at an acute angle of about 10° to 75° to a surface of the microneedle array.

74. The process of any one of embodiments 69 to 73, wherein the light source projects light through the microneedle array at an acute angle of about 30° to 50° to a surface of the microneedle array.

75. The process of any one of embodiments 54 to 74, wherein the observed image is a plurality of shadows projected onto a surface of the microneedle array from said plurality of microneedles.

76. The process of any one of embodiments 54 to 75, wherein the observed image is all the microneedles with an analogous number of microneedle shadows projected on a surface of the microneedle array.

77. The process of any one of embodiments 54 to 76, wherein shadows from said plurality of microneedles do not project onto neighboring microneedles.

78. The process of any one of embodiments 54 to 77, wherein the optical device comprises a spectroscope.

79. The process of any one of embodiments 54 to 78, wherein the optical device comprises a CCD camera.

80. The process of any one of embodiments 54 to 79, wherein the optical device comprises a 2D array camera.

81. The process of any one of embodiments 54 to 80, wherein the optical device comprises a 2D array camera with a telecentric lens.

82. The process of any one of embodiments 54 to 81, wherein the optical device comprises a 2D array camera with a 2× magnification telecentric lens.

83. The process of any one of embodiments 54 to 78, wherein the optical device comprises a 1D linescan camera.

84. The process of any one of embodiments 54 to 82, wherein the optical device is positioned above the microneedle array and a linear line from the optical device through the microneedle array is normal to the array.

85. The process of any one of embodiments 54 to 84, wherein the step of electronically processing said observed image and determining at least one shape parameter further comprises calculating the difference between a theoretical shape of an individual microneedle and an observed shape of the individual microneedle.

86. The process of embodiment 85, wherein the theoretical shape of the individual microneedle is digitally generated.

87. The process of any one of embodiments 54 to 86, wherein the observed image is an 8-bit to 16-bit grayscale image.

88. The process of embodiment 87, further comprising horizontally flat-fielding the observed image to account for variable background intensity.

89. The process of embodiment 87 or 88, further comprising an image sharpening step.

90. The process of any one of embodiments 87 to 89, wherein the image sharpening step comprises an unsharp masking technique.

91. The process of any one of embodiments 87 to 89, wherein the image sharpening step comprises a non-linear deconvolution filter.

92. The process of any one of embodiments 87 to 91, further comprising a binary threshold which segments the plurality of microneedle shadows from said surface on the microneedle array.

93. The process of any one of embodiments 87 to 92, further comprising a blob extraction algorithm to isolate an individual microneedle shadow.

94. The process of embodiment 56, wherein the step of determining an amount of material on said plurality of microneedles further comprises;

defining a coated region from a shadow of an individual microneedle;

mathematically rotating the coated region around a microneedle tip's central axis to form a solid of revolution;

calculating an amount of a first material comprising the solid of revolution;

calculating an amount of a second material comprising an underlying microneedle structure for the coated region; subtracting the amount of the second material from the first material;

thereby determining the amount of said material on said plurality of microneedles.

95. The process of any one of embodiments 54 to 94, wherein said shape parameter is at least one of microneedle height, width, angle, spacing, base area, or combinations thereof.

96. An apparatus for inspecting a microneedle array comprising:

an optical device;

a light source; and a microneedle array comprising a plurality of microneedles with a material coating on a plurality of microneedles;

97. The apparatus of embodiment 96, further comprising an image processing device.

98. The apparatus of embodiment 97, wherein the image processing device is a computer.

99. The apparatus of any one of embodiments 96 to 98, further comprising a surface on which the microneedle array is imaged.

100. The apparatus of any one of embodiments 96 to 99, wherein the optical device is a 2D array camera.

101. The apparatus of any one of embodiments 96 to 100, wherein the light source is a white LED with a collimated lens.

102. A process of inspecting a microneedle array comprising:

illuminating at least a portion of a microneedle array that comprises a plurality of microneedles with a directed light source;

capturing an observed image of said plurality of microneedles using an optical device;

electronically processing the observed image; and determining an amount of a material coating on said plurality of microneedles.

103. The process of embodiment 102, wherein the light source is a white LED.

104. The process of embodiment 102 or 103, wherein the observed image is a plurality of microneedles with a plurality of microneedle shadows projected on a surface of the microneedle array.

105. The process of any one of embodiments 102 to 104, wherein the optical device is a 2D array camera.

106. The process of any one of embodiments 102 to 105, wherein the step of determining an amount of material on said plurality of microneedles further comprises;

defining a coated region from a shadow of an individual microneedle;

mathematically rotating the coated region around a microneedle tip's central axis to form a solid of revolution;

calculating an amount of a first material comprising the solid of revolution;

calculating an amount of a second material comprising an underlying microneedle structure for the coated region;

subtracting the amount of the second material from the first material;

thereby determining the amount of said material on said plurality of microneedles.

EXAMPLES

Normal Incidence Shadow Inspection

Figure 3A:
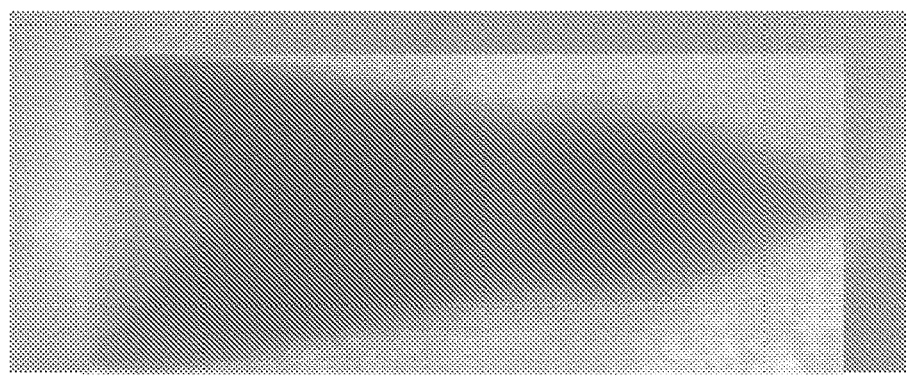
FIG. 3A is an exploded view of a microneedle shadow prior to processing.

Referring to FIG. 1, the microneedle array 100 was supported on a flat surface 104. The optical device 101 used was a 2D array camera equipped with a 2× magnification telecentric lens and oriented above the microneedle array 100 wherein a linear line 106 from the optical device 101 to the microneedle array 100 is normal to the surface of the microneedle array. The microneedle array 100 was illuminated with a LED light source 102 equipped with a collimated lens 103. The light source 102 was positioned such that a linear line 107 from the light source 102 to the surface of the microneedle array 100 was at an acute angle of about 45° to the surface of the microneedle array 100. The patch was also rotated such that the rows of microneedles (shown in FIG. 2) are at a 45° angle from the shadows 111 cast by the microneedles 110. The camera's focal plane was set to the base of the array so that the shadows 111 cast by the microneedles 110 are being in focus. As shown in FIG. 3A, the shadows create a cross-sectional profile of each tip and its ovoid material coating protrusion. The image in FIG. 3A was processed to isolate the shadow from the microneedle array background, giving FIG. 3B. The uncoated microneedle portion 120 is then separated from the coated ovoid region 122. If the sample is perfectly flat, the profile of every tip can be measured in a single image. Additionally, the z-axis cross-section profile is assumed to be rotationally symmetric. Therefore, all the information necessary to calculate the volume of the material coating over the entire patch is available in a single image.

An experiment to optimize the collimated light configuration showed that an angle of about 45° from the base of the patch gives the best shadow signal. A lesser angle (closer to 0° or parallel to microneedle array surface) causes the shadow to overlap the base of the adjacent microneedle and a greater angle (closer to 90° or perpendicular to the surface of the microneedle array) reduces the shadow's area.

Various visible light wavelengths were tested, but none showed significant improvement over broadband white light. Increasing the light level such that the patch background was nearly at saturation improved the contrast of the shadows.

As seen in FIG. 2, the final optical configuration produces images with sharp shadows and very clear protrusions that indicate the presence of the material coating.

Image Processing Algorithm

Once an image has been captured, it can be processed to extract an estimate of the total amount of material present on the patch. A three-step method to was used to extract an estimate of the total amount of material present on the patch. This method is meant to be illustrative and not limiting. The image processing may comprise more or less steps, and even different steps than described herein.

1. Binarize image and extract blobs to identify the shadow of each microneedle tip
2. Find drug coating protrusion on shadow profile
3. Calculate volume of protrusion 1. Isolate Tip Shadows The input image to the first stage of the algorithm was an 8-bit gray scale image of arbitrary size. The image was first horizontally flat-fielded to account for the variable background intensity from the lighting setup. Next, the edges of the shadows were enhanced using an image sharpening technique such as unsharp masking or a non-linear deconvolution filter.

Figure 3B:
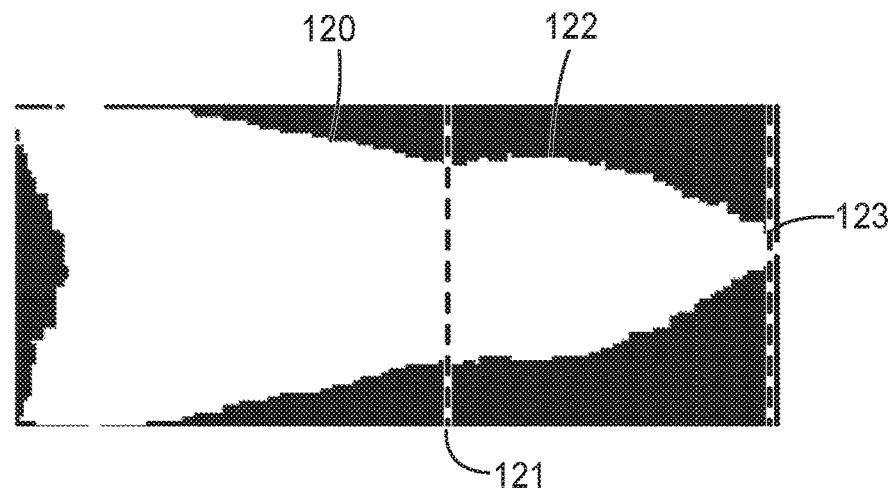
FIG. 3B is an exploded view of a microneedle shadow after processing.

Once the image has been preprocessed, a binary threshold segments the shadows from the background. A blob extraction algorithm was then run to isolate each individual microneedle shadow. The remaining steps described are executed on every tip identified. FIG. 3b shows the results of the binarization on a single microneedle tip.

2. Find Coating Protrusion

Referring to FIG. 3B, the uncoated microneedle portion 120 changes to the material coated ovoid region 122, the two regions divide by dashed line 121. The shadows are cast perfectly horizontal (intentionally set by the camera's orientation), therefore the shadow's profile is created by taking the column-wise sum of the binarized microneedle (see FIG. 3B). Dividing by two converts this result from a measure of the shadow's diameter (in pixels) to a measure of its radius (in pixels), and yields the profile shown in FIG. 4.

Figure 4:
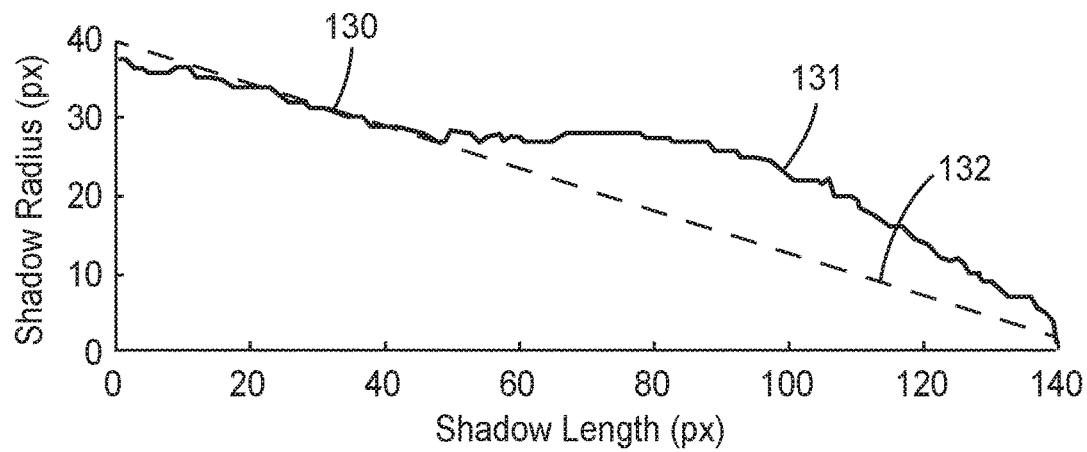
FIG. 4 is a 2-dimensional sectional profile of the microneedle shadow in FIG. 3B.

Once the shadow's profile is found, the algorithm estimates the nominal edge of the uncoated microneedle portion 120. Referring to FIG. 4, it was concluded through manual inspection that the reasonably linear region 130 from 20 to 40 pixels from the base of the shadow's profile contains no material coating. Linear regression was used on the data points within the reasonably linear region 130 to extrapolate the uncoated edge to the tip of the microneedle structure (dotted black line 132 in FIG. 4).

The longest contiguous span 131 of the shadow's profile that exceeded the nominal microneedle edge was determined to be the location of the drug coating (the region between dashed line 121 and microneedle tip 123 in FIG. 3B).

3. Calculate Amount of Material

An estimate of the amount of material on each microneedle is then calculated using the two-dimensional profile of the coating (FIG. 4). First, the coated region is mathematically rotated around the microneedles central axis to form a solid of revolution. The volume of solid of revolution is calculated using the method of discrete disk summation, given in Equation 1 below where "a" is the initial starting point of the summation, "b" is the end point of the summation, and "$r_i$" is the radius of the solid of revolution.

$$V = \pi \Sigma_{i=a}^{b} (r_i^2) \tag{1}$$

However, this volume is not entirely comprised of coating material, so it is necessary to subtract out the underlying microneedle structure. The microneedles used in this example have a pyramidal shape, therefore, the equation for a truncated pyramid with base side widths "a" and "b", and height "h" is given in Equation 2.

$$V = \frac{1}{3}(a^2 + ab + b^2)h \tag{2}$$

The volume for the truncated pyramid is then subtracted from the volume of the solid of revolution. The calculated value is converted from pixels$^3$ to μm$^3$ using the imaging system's spatial resolution (s$^3$) to obtain a volume. The resulting volume is then scaled by the total number of tips (n) on the patch to produce the estimated drug dosage of the entire delivery system. Multiplying by the density (ρ) of the material obtains a total mass of the material coating the microneedle array. The final equation is given below where $r_k$ is the radius of the profile at index k (pixel), $r_f$ is the radius of the profile at the first index f (pixel), $r_l$ is the radius of the profile at the last index l (pixel), l is the last index (pixel), and f is the first index (pixel).

$$M_{material} = ns^3 \rho (V_{bump} - V_{pyramid}) = ns^3 \rho \left( \pi \sum_{k=f}^{l} (r_k^2) - \frac{2}{3}(r_f^2 + r_f r_l + r_l^2)(l-f) \right) \tag{3}$$

4. Experimental Results

The process was validated with twelve microneedle patches coated in the drug abalopartide. Four patches were coated with no drug (0% coating), four with approximately 200 mcg (40% coating), and four with approximately 400 mcg (100% coating). The mass of the drug coating was measured on twenty to thirty tips on each patch using the method already described. Each result was scaled by the total number of tips on the patch (n=316) to produce an estimate of the patch's total drug content based solely on the tip measured.

Figure 5:
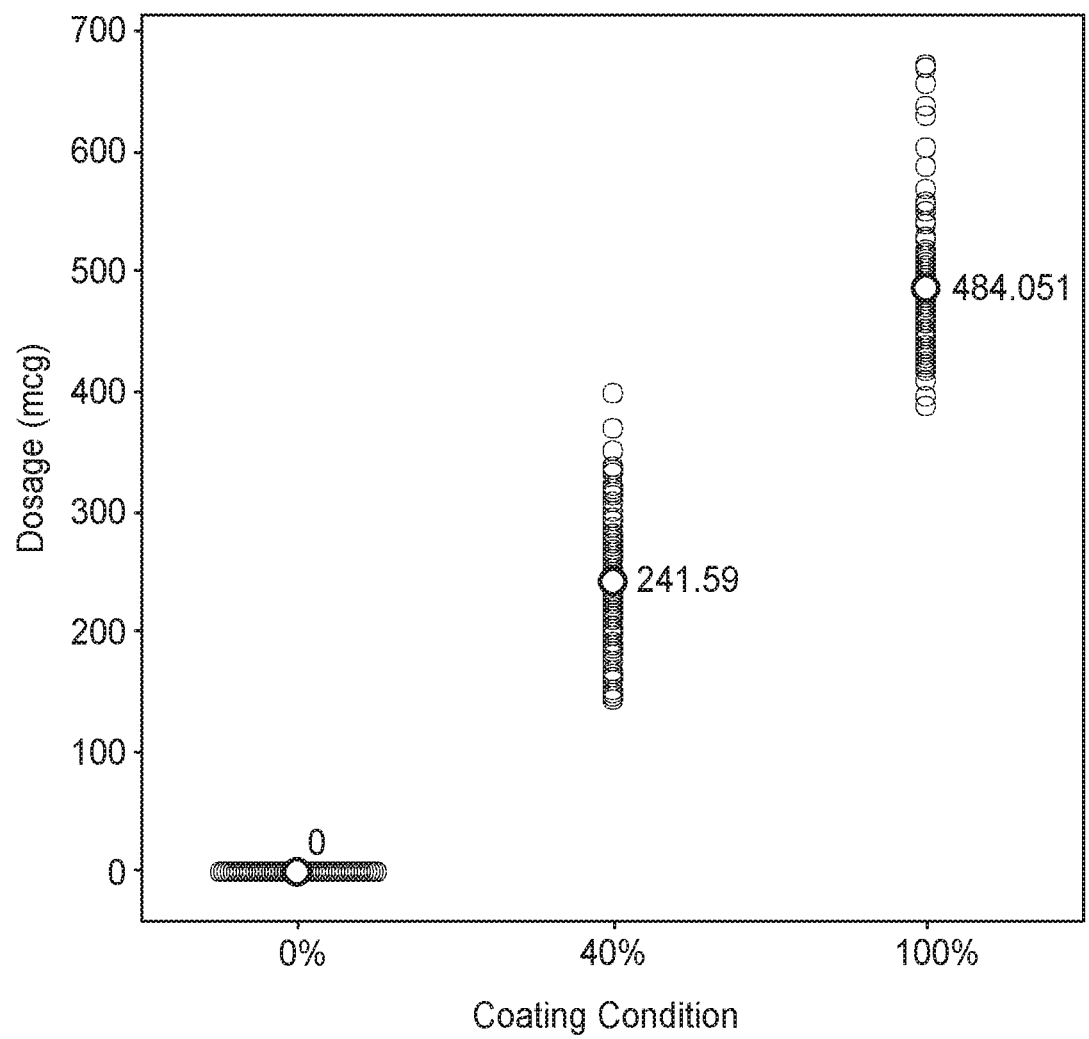
FIG. 5 is a plot of aggregate dosage measurements.
Figure 6:
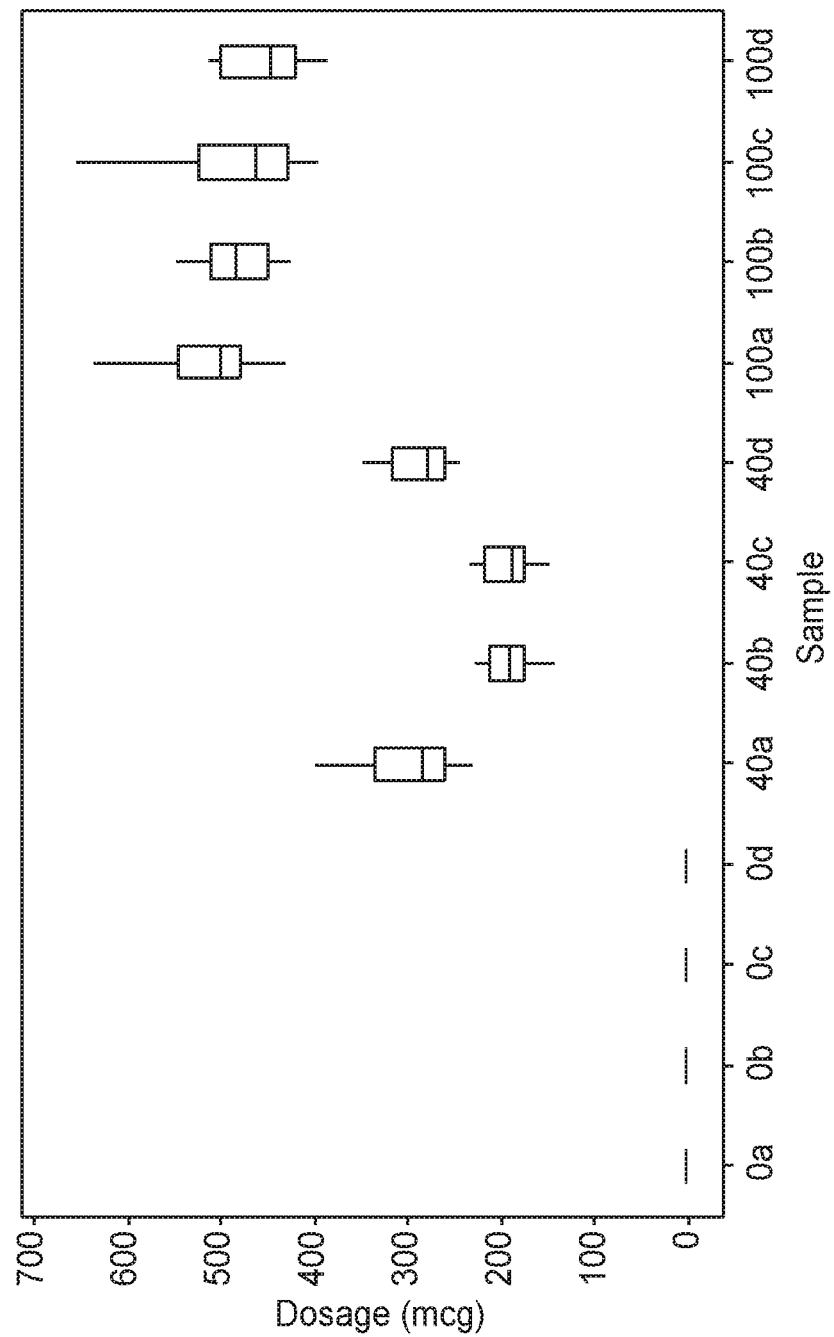
FIG. 6 is a boxplot of measured dosage per patch.

An individual value plot of the aggregate dosage measurements is shown in FIG. 5 and a boxplot of the measured dosage per patch is shown in FIG. 6. These results show a statistically significant difference between the three different coating conditions (P=0.000) and correspond well with the expected drug dosages of the twelve samples.

The complete disclosures of the patents, patent documents and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A process of making a microneedle array comprising:
   providing a microneedle array having a plurality of microneedles of a desired shape;
   illuminating at least a portion of said microneedle array that comprises at least one microneedle;
   capturing an observed image of said at least one microneedle using an optical device, wherein the observed image is at least one shadow projected onto a surface of the microneedle array from the at least one microneedle;
   electronically processing said observed image and determining at least one shape parameter for said at least one microneedle based upon the processed observed image;
   accepting said microneedle array if said at least one shape parameter is within an acceptable range;
   thereby providing a microneedle array that comprises a known shape of the plurality of microneedles.

2. The process of claim 1, wherein said at least one microneedle is coated with a material.

3. The process of claim 2, further comprising determining an amount of material on said at least one microneedle.

4. The process of claim 3, wherein the step of determining an amount of material on said at least one microneedle further comprises;
   defining a coated region from a shadow of an individual microneedle;
   rotating a two-dimensional profile of the coated region around a microneedle tip's central axis to form a solid of revolution;
   calculating an amount of a first material comprising the solid of revolution;
   calculating an amount of a second material comprising an underlying microneedle structure for the coated region;
   subtracting the amount of the second material from the first material;
   thereby determining the amount of said material on said at least one microneedle.

5. The process of claim 1, wherein the step of illuminating further comprises illuminating with a directed light source.

6. The process of claim 5, wherein the light source projects light through the microneedle array at an acute angle of between about 10° and 75° to a surface of the microneedle array.

7. The process of claim 1, wherein said shadows from said at least one microneedle do not project onto neighboring microneedles.

8. The process of claim 1, wherein the optical device comprises a 2D array camera.

9. The process of claim 1, wherein the optical device comprises a 1D linescan camera.

10. The process of claim 1, wherein the optical device is positioned above the microneedle array and a linear line from the optical device through the microneedle array is normal to the array.

11. The process of claim 1, wherein the step of electronically processing said observed image and determining shape parameter further comprises calculating the difference between a theoretical shape of an individual microneedle and an observed shape of the individual microneedle.

12. The process of claim 1, wherein the observed image is an 8-bit to 16-bit grayscale image comprising said at least one microneedle with at least one microneedle shadow projected on a surface of the microneedle array.

13. The process of claim 12, further comprising horizontally flat-fielding the observed image to account for variable background intensity.

14. The process of claim 12, further comprising a binary threshold which segments the plurality of microneedle shadows from said surface on the microneedle array.

15. The process of claim 12, further comprising a blob extraction algorithm to isolate an individual microneedle shadow.

16. The process of claim 1, wherein the shape parameter is at least one of microneedle height, width, angle, spacing, base area, or combinations thereof.

17. A process of inspecting a microneedle array comprising:
    illuminating at least a portion of a microneedle array that comprises at least one coated microneedle with a directed light source;
    capturing an observed image of said at least one coated microneedle using an optical device, wherein the observed image is at least one shadow projected onto a surface of the microneedle array from the at least one coated microneedle;
    electronically processing said observed image; and
    determining an amount of a material coating on said at least one coated microneedle.

18. The process of claim 17, wherein the light source projects light through the microneedle array at an acute angle of between about 10° and 75° to a surface of the microneedle array.

19. The process of claim 17, wherein determining the amount of material on the at least one coated microneedle further comprises:
    defining a coated region from a shadow of an individual microneedle;
    rotating a two-dimensional profile of the coated region around a microneedle tip's central axis to form a solid of revolution;
    calculating an amount of a first material comprising the solid of revolution;
    calculating an amount of a second material comprising an underlying microneedle structure for the coated region;
    subtracting the amount of the second material from the first material;

thereby determining the amount of the material on the at least one coated microneedle.

* * * * *